United States Patent
Kang et al.

(10) Patent No.: US 6,184,346 B1
(45) Date of Patent: Feb. 6, 2001

(54) PROTEASE INHIBITORS DERIVED FROM GUAMERIN

(75) Inventors: Ke-Won Kang; Dong-Ryoung Kim, both of Taejon (KR)

(73) Assignee: Korea Advanced Institute of Science and Technology (KR)

( * ) Notice: Under 35 U.S.C. 154(b), the term of this patent shall be extended for 0 days.

(21) Appl. No.: 09/068,624

(22) PCT Filed: Mar. 11, 1997

(86) PCT No.: PCT/KR97/00036

§ 371 Date: May 7, 1998

§ 102(e) Date: May 7, 1998

(87) PCT Pub. No.: WO98/09993

PCT Pub. Date: Mar. 12, 1998

(30) Foreign Application Priority Data

Sep. 9, 1996 (KR) .................................................. 96-38844

(51) Int. Cl.[7] .............................. A61K 38/04; C12N 9/00; C12N 9/66; C12N 9/56
(52) U.S. Cl. ............................ 530/326; 530/324; 514/13; 514/2; 514/12; 435/184; 435/212; 435/218; 435/219; 435/183; 435/222
(58) Field of Search .................................... 435/184, 212, 435/218, 219, 222; 530/324, 325–328; 514/13, 2, 12

(56) References Cited

U.S. PATENT DOCUMENTS 6,008,320 * 12/1999 Kang et al. ........................... 530/324

FOREIGN PATENT DOCUMENTS 28 08 396    9/1979 (DE) .
90/12808    11/1990 (WO) .

OTHER PUBLICATIONS

Kim et al. "Guamerin–derived synthetic inhibitors against elastase and subtilisin," Protein Pep. Lett. (Oct. 1996) 3(5): 301–308.*

Isolation and Characterization of Guamerin, a New Human Leukocyte Elastase inhibitor from Hirudo nipponia, Hyo H. Jung, et al. The Journal of Biological Chemistry vol. 270, No. 23, Issue of June 9, pp. 13879–13884, 1995.

* cited by examiner

*Primary Examiner*—Christopher Tate
(74) *Attorney, Agent, or Firm*—Knobbe Martens Olson & Bear LLP

(57) ABSTRACT

The present invention relates to peptides inhibiting elastase and subtilisin activity, which are derived from Guamerin, an elastase-inhibiting protein isolated from a Korean leech, Guameri(Hirudo nipponia). Since the peptides of the invention permit their convenient synthesis and use, it can be applied for the development of elastase- and subtilisin-inhibiting agents. Also, since the dimeric peptides of the invention have strong elastase- and subtilisin-inhibiting activities, they can be more practically applied for the treatment of diseases associated with elastase and subtilisin. Moreover, all of the peptides of the invention can be safely used for human body as a potential drug, since they have relatively lower molecular weights.

4 Claims, 2 Drawing Sheets

| Peptide | Amino acid sequence |
|---|---|
| Guamerin | VDENAEDTHGLCGEKTCSPAQVCLNNECACTAIRCMIFCPNGFKVDENGCEYPCTCA |
| pM | TAIRCMIFCPNGFKVDENG |
| pR | TAIRCRIFCPNGFKVDENG |

*Fig. 1*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 57 amino acids
      (B) TYPE: amino acid (C) STRANDEDNESS: single
        (D) TOPOLOGY: linear (ii) MOLECULE TYPE: protein (xi) SEQUENCE DESCRIPTION: SEQ ID NO:1:

Val Asp Glu Asn Ala Glu Asp Thr His Gly Leu Cys Gly Lys Thr
1               5                   10                  15

Cys Ser Pro Ala Gln Val Cys Leu Asn Asn Glu Cys Ala Cys Thr Ala
            20                  25                  30

Ile Arg Cys Met Ile Phe Cys Pro Asn Gly Phe Lys Val Asp Glu Asn
        35                  40                  45

Gly Cys Glu Tyr Pro Cys Thr Cys Ala
    50                  55

(2) INFORMATION FOR SEQ ID NO:2:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Thr Ala Ile Arg Cys Met Ile Phe Cys Pro Asn Gly Phe Lys Val Asp
1               5                   10                  15

Glu Asn Gly (2) INFORMATION FOR SEQ ID NO:3:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Thr Ala Ile Arg Cys Arg Ile Phe Cys Pro Asn Gly Phe Lys Val Asp
1               5                   10                  15

Glu Asn Gly

PROTEASE INHIBITORS DERIVED FROM GUAMERIN

This is a 35 U.S.C. § 371 application of PCT/KR97/00036, filed Mar. 11, 1997.

BACKGROUND OF THE INVENTION

1. Field of the Invention

The present invention relates to peptides derived from Guamerin which inhibit protease activity, more specifically, to peptides inhibiting elastase and subtilisin activity, which are derived from Guamerin, an elastase-inhibiting protein isolated from a Korean leech, Guameri(Hirudo nipponia).

2. Description of the Prior Art

Elastase is a serine protease capable of degrading mainly elastin and also connective tissue proteins such as collagen, cartilage, and fibronectin(see: Reilly, C. et al., Biochem. Biophys. Acta., 621:147–167(1980); Mainardi, C. L. et al., J. Biol. Chem., 255:5436–5441(1980)).

Human leukocyte elastase is stored principally in neutrophils and the stored elastase is released, when neutrophils encounter foreign pathogens or antigens in blood, to degrade them so that body is protected from the harmful factors(see: Weisemann, G. et al., New Engl. J. Med., 303:27–34(1980)). However, uncontrolled secretion of elastase which frequently results from aging of the cells or genetic disorder may cause non-specific proteolysis and trigger destructive processes associated with various chronic diseases such as rheumatoid arthritis, emphysema, and psoriasis(see: Glinski, W. et al., J. Invest. Dermatol., 75:481–487(1980); Snider, G. L., Med. Clin. North. Am., 65:647–666(1981)).

In medical field, for the treatment of said diseases, strenuous efforts have been made in developing an agent which can effectively suppress the activity of elastase which is released abnormally in excess from the tissues of joint cartilage, lung, and skin. As a consequence, elastase-inhibiting proteins have been isolated from a variety of biological sources such as birds including turkeys or ducks, European leeches, and human skin(see: Schalwijk, J. et al., Br. J. Dermatol., 1512:181–186(1986).; Wlodow, O. et al., J. Biol. Chem., 165:14791–14796(1990); Hochstrasser, K. et al., Hopps-Seyler's Z. Physiol. Chem., 362:1369–1375 (1981); Seemiller, U. et al., Hopps-Seyler's z. Physiol. Chem., 361:1841–1846(1980)), which were found to be effective for the treatment of said diseases, especially when a medicine containing the protein as an active ingredient was administered directly to the affected parts.

However, the elastase-inhibiting proteins of prior art, except the one isolated from human skin, have had trouble for the use as a medicine, since their specificity for elastase is so low that the activities of other enzymes are possibly inhibited. Moreover, since the said elastase-inhibiting proteins including the one from human skin have an extremely high molecular weight, a serious problem has been frequently encountered that the proteins may be easily denatured by heat, which finally decreases their activities rapidly.

Under the circumstances, there are strong reasons for exploring and developing alternative proteins which inhibit the elastase activity in a specific manner. In this connection, the present inventors have isolated a novel elastase-inhibiting protein named 'Guamerin', from a Korean leech, Guameri(Hirudo nipponia) and discovered that Guamerin inhibits the elastase activity specifically, has stronger activity than the conventional elastase-inhibiting proteins, and is also stable under strongly acidic or alkaline condition(see: UK Patent Application GB 2300190A; H. I. Jung et al., J. Biol. Chem., 270(23) :13879–13884(1995)). Accordingly, Guamerin has a distinction over the conventional elastase-inhibiting proteins that: it may not cause untoward effects, when it is administrated as a medicine; and, its chemical nature is so stable that it is not easily denatured in the course of mass production, storage and transport, which naturally eases its practical application.

However, since Guamerin is still large molecule to be practically applied in medicinal use, the inventors have made an effort to develop peptides which contain active sites of Guamerin showing elastase-inhibiting activities permitting its convenient synthesis and use.

SUMMARY OF THE INVENTION

In accordance with the present invention, the inventors discovered that: peptides consisting of 19 amino acids which contain the 36th-methionine of the active site of Guamerin, show elastase-inhibiting activities; and, the said peptides, unlike an intact Guamerin, also inhibit subtilisin activity and elastase activity as well.

A primary object of the invention is, therefore, to provide peptides derived from Guamerin which inhibit elastase and subtilisin activities.

The other object of the invention is to provide dimeric peptides formed by intermolecular disulfide bond between the peptides, which also inhibit elastase and subtilisin activities.

BRIEF DESCRIPTION OF THE DRAWINGS

The above and the other objects and features of the present invention will become apparent from the following descriptions given in conjunction with the accompanying drawings, in which:

FIG. 1 is the amino acid sequences of Guamerin(SEQ ID NO:1) and two peptides derived therefrom, i.e., pM and pR(SEQ ID NO:2 and SEQ ID NO:3).

DETAILED DESCRIPTION OF THE INVENTION

Figure 2A:
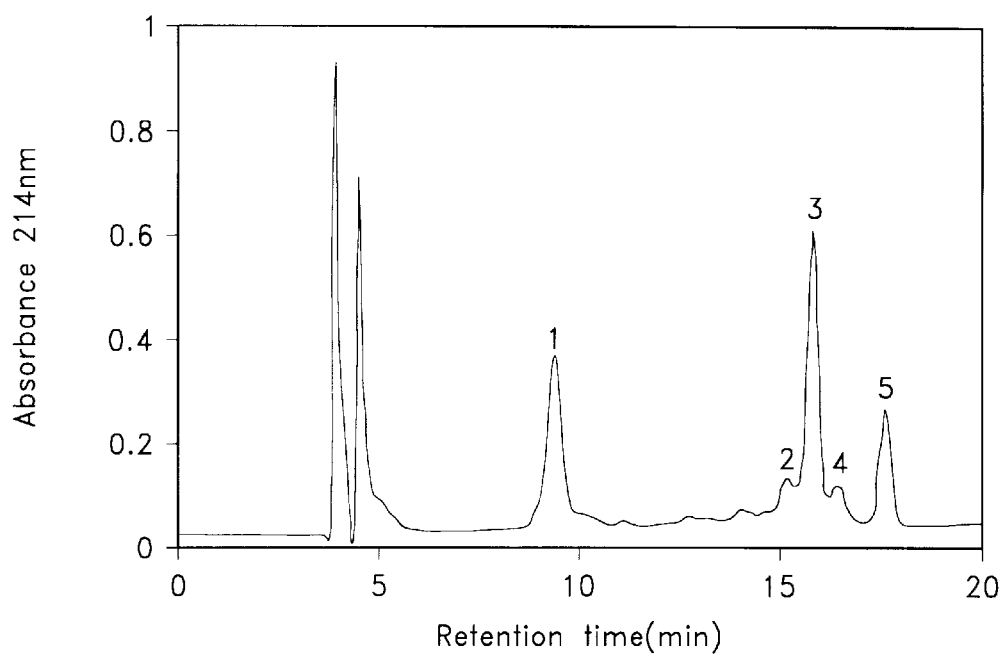
FIGS. 2(A) and 2(B) represent HPLC patterns of two synthetic peptides of the invention, i.e., pM and pR, after oxidoreductive reaction.

The present inventors purified an elastase-inhibiting protein, i.e., Guamerin, from fully matured leeches collected in Korea, by a series of isolation steps including acetone extraction, gel filtration, anion-exchange chromatography and reverse-phase HPLC(high performance licuid chromatography). Guamerin was found to be a protein of a molecular weight of 6,110 Da which is composed of 57 amino acid residues(see: FIG. 1) Further, it was determined that: Guamerin contains 10 cysteine residues which are required for the formation of disulfide bond permitting rigid structure of a protein; and, its active site is occupied with a methionine residue at the 36th position and an isoleucine residue at the 37th position, respectively(see: UK Patent Application GB 2300190A; H. I. Jung et al., J. Biol. Chem., 270(23) :13879–13884(1995)).

The present inventors, in order to develop short peptides which afford their convenient synthesis and use, while possessing the same activities of Guamerin, have synthesized two peptides as followings: a peptide(pM) consisting of 19 amino acids in which the 36th-methionine or the active site of Guamerin, is Positioned at the center; and, a peptide (pR) having the same amino acid sequence as the said pM except for arginine substituted for the 36th-methionine said peptides may be synthesized by chemical means or by employing DNA manipulation techniques conventional in the art.

Determination of biochemical activities has proved that: the two synthesized peptides show inhibitory activities against only elastase and subtilisin among various protease; and, inhibitory activity of the short peptide is not changed, even though the 36th-methionin is substituted with other amino acid. Therefore, it was concluded that the said peptides can be used as active ingredients for potential elastase- and subtilisin-inhibiting agents.

On the other hand, since disulfide bond formed by cross-linking of cysteines may affect protein structure which is critical to their activities, oxidoreductive reaction was carried out to form disulfide bonds in the synthesized peptides. Then, the oxidoreduced peptides were isolated, and their protease-inhibiting activities and molecular weights were determined. As a result, it was found that dimeric peptides formed by intermolecular disulfide bond between the monomers, by the oxidoreductive reaction, have much stronger elastase- and subtilisin-inhibiting activities than the monomers. Particularly, it was found that the dimeric peptides have elastase-inhibiting activities almost the same as that of Guamerin, and very high subtilisin-inhibiting activities unlike Guamerin.

Accordingly, since the dimeric peptides of the invention have strong elastase- and subtilisin-inhibiting activities and can be synthesized by convenient means, they may be more practically applied for the treatment of diseases associated with elastase and subtilisin, when compared to Guamerin. Moreover, they can be safely used for human body as a potential drug, since they have relatively lower molecular weights.

The present invention is further illustrated in the following examples, which should not be taken to limit the scope of the invention. Particularly, in accordance with the purposes of the invention, all Guamerin-derived monomeric and dimeric peptides having protease-inhibiting activities should be fallen within the scope of the present invention, in addition to monomeric and dimeric pM and pR described in the following examples which have elastase- and subtilisin-inhibiting activities.

EXAMPLE 1

Purification and characterization of Guamerin

Fully matured leeches collected in Korea were treated with 95% (v/v) ethyl alcohol to remove stomach impurities and blood clot. Then, they were put in 80% (v/v) acetone and homogenized to prepare acetone extract. The acetone extract was concentrated and applied on a Sephadex G-75 column (Sigma, USA). After washing the column, fractions showing the elastase-inhibiting activity were pooled and applied on a DEAE-Sepharose column(Sigma, USA). After washing and eluting the column, fractions showing the elastase-inhibiting activity were pooled, concentrated and applied on a reverse-phase HPLC column(Delta-pak C18, Millipore, USA). Thus, Guamerin, an elastase-inhibiting protein was finally purified.

As a result of analyses of molecular weight and amino acid sequence, it was found that: Guamerin is a protein of molecular weight of 6,100 Da which is composed of 57 amino acid residues; and, it contains 10 cysteine residues which are required for formation of disulfide bond permitting rigid structure of a protein(see: FIG. 1). Also, it was determined that the active site of Guamerin includes 36th-methionine and 37th-isoleucine, and Guamerin retains an inihibiting-activity highly specific to elastase. Moreover, it was found that Guamerin shows stability against heat as well as strong acids and alkalies.

EXAMPLE 2

Chemical synthesis of peptides derived from Guamerin and determination of their activities In order to synthesize short peptides having the same activities of Guamerin, peptides consisting of 19 amino acids in which 36th-methionine residue of the active site of Guamerin is located in the center, were designed. Then, two peptides, i.e., pM and pR, were synthesized chemically, based on the amino acid sequence of Guamerin(SEQ ID NO:1) disclosed in FIG. 1. In FIG. 1, pM is a peptide having the amino acid sequence(SEQ ID NO:2) from 31th-threonine to 49th-glycine of Guamerin, and pR is a peptide having the same amino acid sequence as pM except for 36th-methionine substituted with arginine(SEQ ID NO:3). The two peptides were designed so that they contain two cysteines near the active site, which, in turn, provide disulfide bond formed by cross-linking to give a desired active product whose chemical structure was stabilized.

The synthesized peptides were applied on a reverse-phase HPLC column, and purified by elusion with a linear gradient of acetonitrile containing 0.1% trifluoroacetic acid. The activities of the purified peptides were determined, based on the inhibitory activities against degradation of a substrate, i.e., azocasein, by various kinds of protease such as trypsin, chymotrypsin, subtilisin and elastase, while controlling the concentrations of a peptide and a protease at a ratio of 20:1 (w/v). As a result, it was found that the synthetic peptides show inhibitory activities against only elastase and subtilisin, whose percentage of maximum inhibition is 7 to 9%(see: Table 2).

EXAMPLE 3

Determination of activities of peptide dimers formed by disulfide bond

Since two cysteines of the synthetic peptides may affect the activities of the peptides, effects of disulfide bonds in the peptides(i.e., pM and pR), was studied after carrying out oxidoreductive reaction of the cysteine residues. In this connection, the oxidoreductive reaction was carried out by incubating the peptides in 0.1 M sodium acetate buffer(pH 7.8) containing 1 M guanidine hydrochloride with 0.2 mM oxidized glutathione(GSSG) and 1mM reduced glutathione (GSH) for 2 hours at 37° C.

Figure 2B:
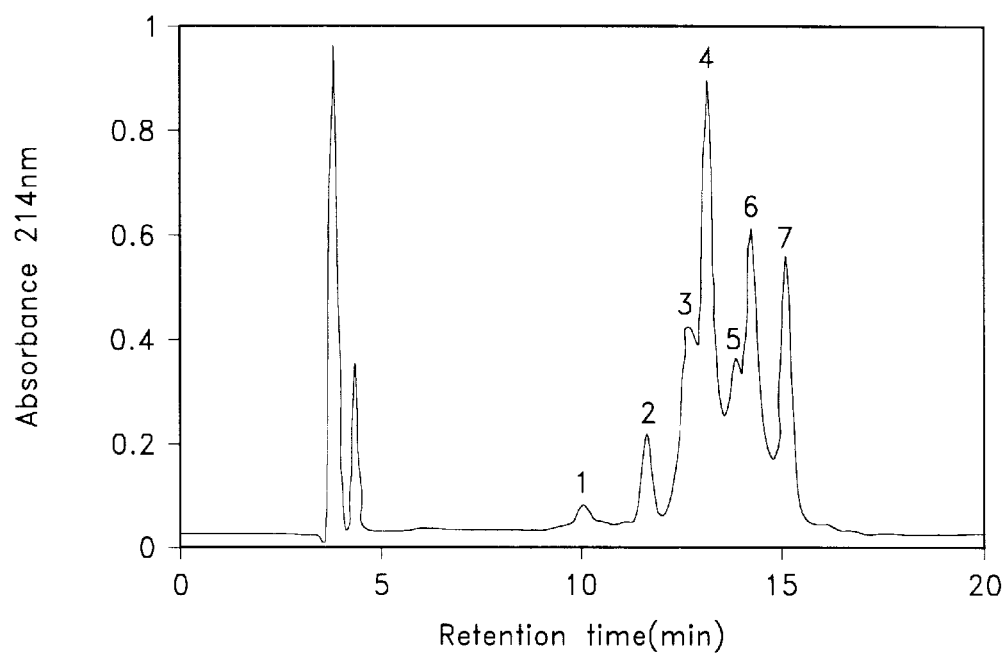

The oxidoreduced peptides were isolated by employing the HPLC column used in Example 2(see: FIGS. 2(A) and 2(B)). FIGS. 2(A) and 2(B) represent HPLC patterns of the synthetic peptides, i.e., pM and pR, respectively, after the oxidoreductive reaction. As shown in FIGS. 2(A) and 2(B), there were five peptides derived from the synthetic peptide of pM, and the peptides corresponding to peaks were named pM(1), pM(2), pM(3), pM(4) and pM(5), respectively. Also, there were seven peptides derived from the synthetic peptide of pR, and the peptides corresponding to peaks were named pR(1), pR(2), pR(3), pR(4), pR(5), pR(6) and pR(7), respectively.

Then, elastase- and subtilisin-inhibiting activities of the isolated peptides were assayed, and molecular types of the peptides were determined by the aid of matrix-assisted laser desorption ionization(MALDI) mass spectrometry. The results were summarized in Table 1 below.

TABLE 1

Types and protease-inhibiting activities of synthetic peptides(*)

| Peptide | Molecular type | Inhibitory activity | |
|---|---|---|---|
| | | Elastase | Subtilisin |
| pM(1) | N.D. | N.D. | N.D. |
| pM(2) | dimer | +++ | +++ |
| pM(3) | dimer | +++ | +++ |
| pM(4) | dimer | +++ | +++ |
| pM(5) | monomer | + | + |
| pR(1) | N.D. | N.D. | N.D. |
| pR(2) | N.D. | N.D. | N.D. |
| pR(3) | dimer | +++ | +++ |
| pR(4) | dimer | +++ | +++ |
| pR(5) | monomer | + | + |
| pR(6) | dimer | +++ | +++ |
| pR(7) | monomer | + | + |

*N.D.: not detected
(+++) and (+) indicate strong and weak activities, respectively.

As can be seen in Table 1, it was found that the peptides showing strong (high) elastase- and subtilisin-inhibiting activities are dimers of pM and pR peptides each of which is derived from the synthetic peptides. Therefore, it was clearly demonstrated that oxidoreductive reaction of monomeric peptides pM and pR provides dimers to possess much stronger elastase- and subtilisin-inhibiting activities than the monomers.

Further, in order to compare various protease-inhibiting activities of the dimers with those of Guamerin and monomeric peptides derived therefrom(i.e., pM and pR), their inhibitory activities against trypsin, chymotrypsin, subtilisin and elastase were determined in the same manner as in Example 1(see: Table 2). In Table 2, pM-D and pR-D indicate dimers of pM and pR, respectively, and pM-PE indicates a peptide where -SH group of cysteine in pM peptide is pyridylethylated.

TABLE 2

Protease-inhibiting activities or Guamerin and the synthetic peptides of the invention

| Peptide | Percentage of maximum inhibition (%) | | | | Inhibitory constant | |
|---|---|---|---|---|---|---|
| | Elastase | Subtilisin | Trypsin | Chymo-Trypsin | Elastase | Subtilisin |
| Guamerin | 82 | 8 | 6 | 7 | 0.81 fM | — |
| pM-D | 86 | 97 | N.D. | N.D. | 49 nM | 31 nM |

TABLE 2-continued

Protease-inhibiting activities or Guamerin and the synthetic peptides of the invention

| Peptide | Percentage of maximum inhibition (%) | | | | Inhibitory constant | |
|---|---|---|---|---|---|---|
| | Elastase | Subtilisin | Trypsin | Chymo-Trypsin | Elastase | Subtilisin |
| pM | 7 | 8 | N.D. | N.D. | — | — |
| pM-PE | N.D. | N.D. | N.D. | N.D. | — | — |
| pR-O | 82 | 91 | N.D. | N.D. | 54 nM | 38 nM |
| pR | 8 | 9 | N.D. | N.D. | — | — |

*N.D. : not detected

As can be seen in Table 2, it was found that dimeric peptides have much stronger elastase- and subtilisin-inhibiting activities than monomers, that is, their percentage of maximum inhibition were determined as 82 to 97%, respectively. Particularly, it was determined that dimeric peptides have elastase-inhibiting activities almost the same as that of Guamerin, and they have very high subtilisin-inhibiting activities unlike Guamerin.

In addition, in order to obtain inhibitory constants of the dimers against elastase, inhibitory activities of the dimers against degradation of a chromogenic peptide substrate, N-succinyl-L-Ala-Ala-p-nitroanilide by elastase, were determined. As a result, it was found that inhibitory constants of- the dimers, i.e., pM-D and pR-D, were 49 nM and 54 nM, respectively(see: Table 2). Also, inhibitory constants of the dimers against subtilisin were determined in the same manner using N-succinyl-L-Ala-Ala-Pro-Phe-p-nitroanilide as a chromogenic peptide substrate. As a result, it was found that inhibitory constants of the pM-D and pR-D were 31 nM and 38 mM, respectively(see: Table 2). Though inhibitory constants of the dimers against elastase and subtilisin show higher values than that of Guamerin against elastase(0.81 fM), they show significant values compared to the conventional inhibitory agents.

As clearly illustrated and demonstrated as aboves, the present invention provides peptides which inhibit elastase and subtilisin activity, which are derived from Guamerin isolated from a Korean leech, Guameri(Hirudo nipconia). Since the peptides of the invention permit their convenient synthesis and use, it can be applied for the development of elastase- and subtilisin-inhibiting agents. Also, since the dimeric peptides of the invention have strong elastase- and subtilisin-inhibiting activities, they can be more practically applied for the treatment of diseases associated with elastase and subtilisin. Moreover, they can be safely used for human body as a potential drug, since they have relatively lower molecular weights.

What is claimed is:

1. An isolated peptide consisting of the amino acid sequence listed as SEQ ID NO: 2, said peptide having inhibitory activity against elastase and subtilisin.

2. An isolated peptide consisting essentially of the amino acid sequence listed as SEQ ID NO:3, said peptide having inhibitory activity against elastase and subtilisin.

3. An isolated dimeric peptide which inhibits elastase and subtilisin activity, wherein said dimeric peptide is formed by an intermolecular disulfide bond between two peptides wherein each of the two peptides consist essentially of SEQ ID NO: 3.

4. An isolated dimeric peptide which highly inhibits elastase and subtilisin activity, wherein said dimeric peptide is formed by an intermolecular disulfide bond between two peptides wherein each of the two peptides consist essentially of SEQ ID NO: 2.

* * * * *